United States Patent [19]
Ly

[11] Patent Number: 5,168,042
[45] Date of Patent: * Dec. 1, 1992

[54] INSTRUMENTLESS QUANTITATIVE ANALYSIS SYSTEM

[76] Inventor: Uy-Vu Ly, P.O. Box 32564, San Jose, Calif. 95152

[*] Notice: The portion of the term of this patent subsequent to Mar. 31, 2004 has been disclaimed.

[21] Appl. No.: 491,357

[22] Filed: Mar. 9, 1990

Related U.S. Application Data

[63] Continuation of Ser. No. 75,244, Jul. 15, 1987, Pat. No. 4,923,800, which is a continuation of Ser. No. 693,739, Jan. 23, 1985, abandoned, which is a continuation-in-part of Ser. No. 569,891, Jan. 10, 1984, Pat. No. 4,654,310.

[51] Int. Cl.⁵ .............................................. C12Q 1/28
[52] U.S. Cl. ........................................ 435/7.1; 422/56; 422/61; 435/4; 435/28; 436/64; 436/69; 436/95; 436/174
[58] Field of Search ................. 422/56, 57, 58, 61; 436/95, 64, 69, 174; 435/4, 7, 28, 805

[56] References Cited
U.S. PATENT DOCUMENTS

| | | |
|---|---|---|
| 3,272,319 | 9/1966 | Brewer .................... 422/61 |
| 3,449,081 | 6/1969 | Hughes ................... 422/61 |
| 3,723,064 | 3/1973 | Liotta ..................... 422/56 |
| 3,917,453 | 11/1975 | Miligan et al. ............ 422/56 |
| 3,964,871 | 6/1976 | Hochstrasser ............. 435/805 |
| 3,983,005 | 9/1976 | Goodhue et al. .......... 435/805 |
| 4,042,329 | 8/1977 | Hochstrasser ............. 436/165 |
| 4,281,062 | 6/1981 | Kallis ...................... 422/56 |
| 4,330,299 | 5/1982 | Cerami .................... 422/56 |
| 4,452,887 | 6/1984 | Kitajma et al. ............ 435/805 |

Primary Examiner—Robert J. Warden
Assistant Examiner—Timothy M. McMahon
Attorney, Agent, or Firm—Morrison & Foerster

[57] ABSTRACT

A general and versatile method for quantitation of a variety of analytes which supplies a directly observable result not requiring instrumentation is disclosed. The method is based on competing enzymic reactions, wherein one of the reactions is capable of forming a directly observable product, which is a colored product. Direct quantitation is obtained by altering the relative amount of competing reaction catalyst with respect to control reaction catalyst. Materials capable of analysis using this method include enzyme substrates, enzymes, immunogens, and specific affinity binding partners.

9 Claims, 4 Drawing Sheets

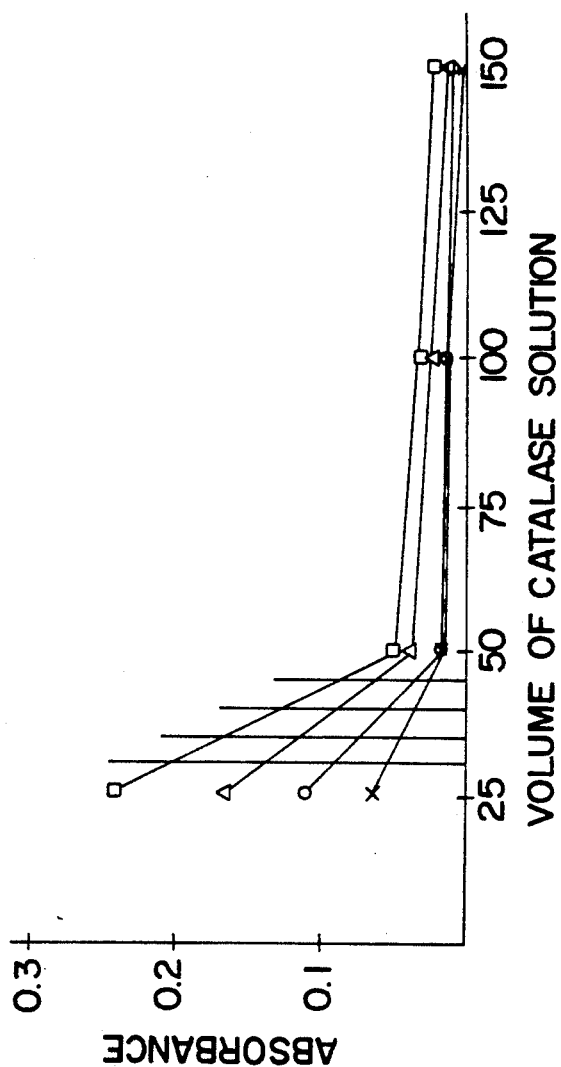

$E_1$ = PEROXIDASE ▲ = ANTIGEN
$E_2$ = CATALASE ◂—$E_2$ = ANTIGEN—$E_2$ CONJUGATE $E_1$ = PEROXIDASE   $E_2$ = CATALASE $E_1$ = CATALASE
$E_2$ = PEROXIDASE
◇ = ANTIGEN
〉—$E_2$ = ANTIBODY–$E_2$ CONJUGATE

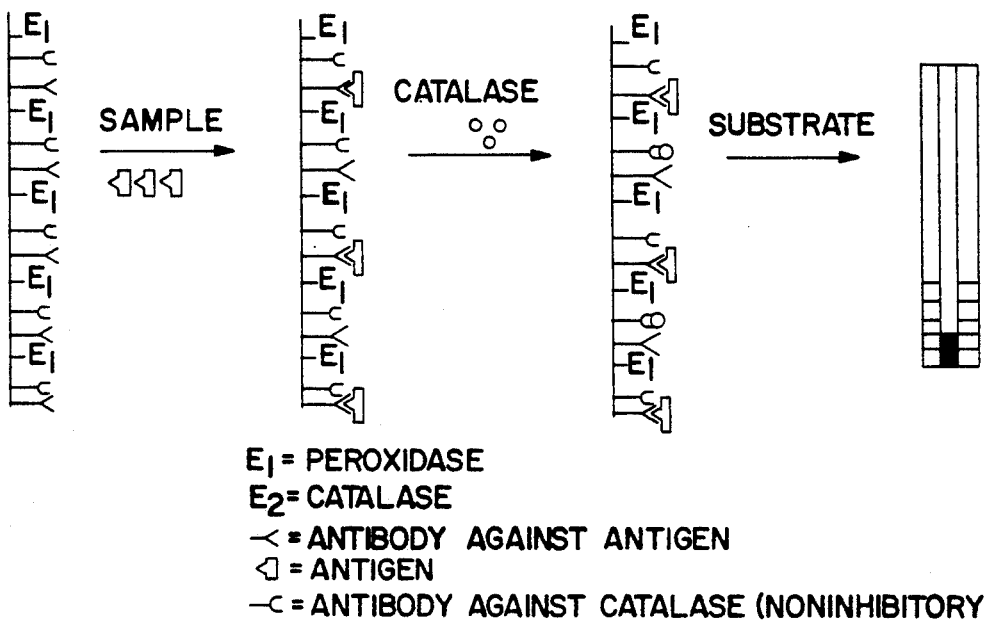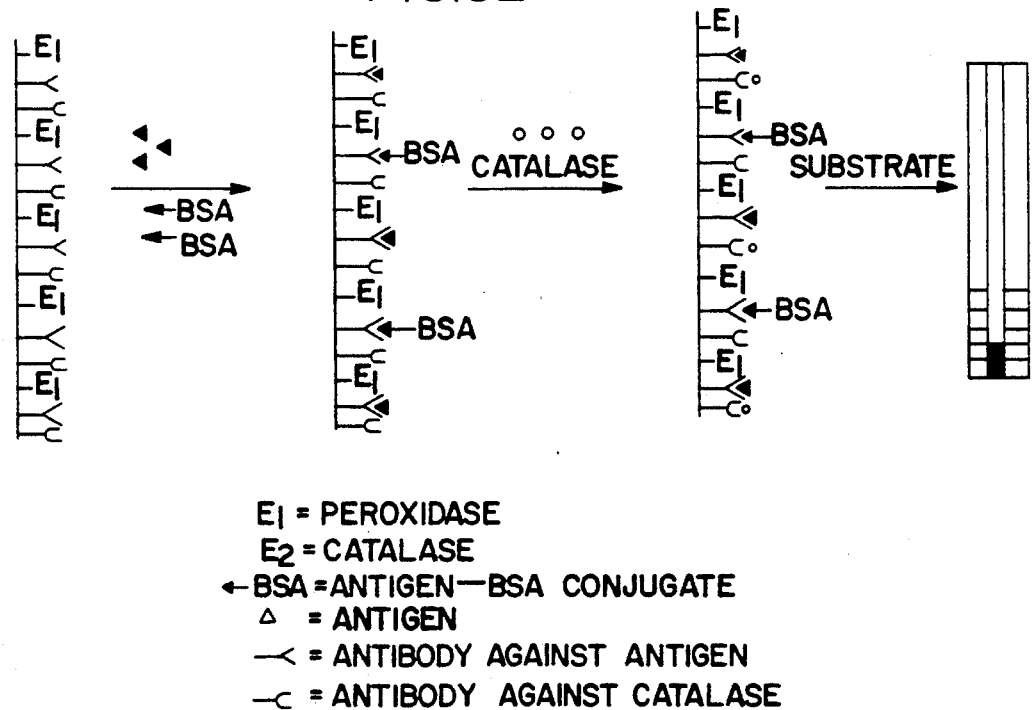

INSTRUMENTLESS QUANTITATIVE ANALYSIS SYSTEM

CROSS-REFERENCE TO RELATED APPLICATIONS

This application is a continuation of U.S. Ser. No. 075,244, filed Jul. 15, 1987 and now issued as U.S. Pat. No. 4,923,800, which is a continuation of U.S. Ser. No. 693,739, filed Jan. 23, 1985, now abandoned, which is a continuation-in-part of U.S. Ser. No. 569,891, filed Jan. 10, 1984 and now issued as U.S. Pat. No. 4,654,310.

TECHNICAL FIELD

The field of the invention is the facile analysis of analytical samples. More particularly, the present invention relates to assessment of the quantity of a desired analyte using a series of competing reactions, wherein a catalyzed control reaction is placed in competition with a second competing catalyzed reaction utilizing the same substrate as the control reaction.

BACKGROUND ART

The need for quantitative determination of the concentration of a substance of interest in a test sample is widespread and varied in application. Such need arises prominently in connection with clinical laboratory tests, quality control in the production of any mixture of materials, for example, food, agricultural or other mixtures; and in analytical assessment of, for example, waste products such as industrial or municipal waste. Methods of quantitation are varied but generally involve generation of some detectable material such as a colored substance, a substance absorbing ultraviolet or infrared light at a particular wavelength, a fluorescent material, or, in general, a material which absorbs or generates radiation of particular energy. Such radiation levels can be detected through instrumentation using instruments of complexity ranging from that of a simple colorimeter, or even a color comparator chart, to sophisticated variable wavelength specific infrared spectrometers. Additional detection methods rely on characteristic properties of either the substance to be determined or of a material into which it can be converted, which are assessed by more complex means, as, for example, mass spectroscopy, nuclear magnetic resonance spectroscopy, or stimulated emission of x-radiation.

The expense and complexity of these analytical procedures are, of course, proportional to the sophistication of the instrumentation required (although a highly complex instrument can sometimes eliminate many operator manipulations). Especially for preliminary screening tests, and for tests which are useful to individual consumers, it would be desirable to formulate testing procedures which obviate the need for expensive instrumentation and which are simple to perform. The present invention provides a method for quantitation of desired analytes which eliminates the need for such complication and expense. It provides a testing method which is usable unaided by instrumentally based analog measurements and gives a digital readout useable to virtually anyone.

An attempt has been made to obtain a digital readout in tests for glucose using a series of oxidation reactions containing varying amounts of reducing agent to prevent the formation of an oxidized indicator, as disclosed by Hochstrasser in U.S. Pat. No. 3,964,871. However, this method is limited to analytes which are capable of generating peroxide, and even for these analytes the results cannot be finely tuned to a desired level of quantitation.

The method of the present invention is grounded on the combination and integration of two concepts, the competition for a substrate by each of a pair of catalysts, and an orderly array of varying levels of competition. The competition aspect per se thus differs from that of, for example, antigen for antibody as in radioimmunoassay (RIA) or enzyme labeled immunosorbent assay (ELISA).

Recently, the use of two enzymes simultaneously has been applied to the problems of extending the range of analyte concentration which can be assessed (German patent application Publication No. DE 3211167A1, published Sep. 29, 1983). The catalysts used in this disclosure were employed in such a way that a cofactor for one catalyst having a detectable product was used up substantially below the level represented by the cofactor for the other, so that the analyte range measured by one catalyst was different from that measured by the other. No means for digital readout was provided, and no advantage was taken of competition, as the two catalysts function substantially independently.

The present invention relies on competition for substrate, as the amount of substrate available for a control reaction is dependent on the relative amount of catalyst for a competing reaction present. In addition, by serially varying the relative amount of competing reaction catalyst the amount of substrate remaining can be left at a detectable level or not. As the relative amount of competing catalyst can be determined by the will of the experimenter (or by a series of pre-set levels chosen by the manufacturer), no instrumentation is required for its quantitation.

DISCLOSURE OF THE INVENTION

The invention provides a method for quantitating the concentration of any desired analyte by assessing a pattern of yes/no responses. Since this is a digital result, it can be read directly using a series of, for example, test papers, or pattern on a matrix, rather than by use of expensive instrumentation or even a comparator. The method which is represented by this aspect of the invention comprises testing a sample by means of, in the simplest example, an indicator reaction in varying levels of competition with a competing reaction for the same analyte. Thus, one can assess by a series of positive or negative responses, at what level of analyte the indicator begins to lose. More analyte will require more competition before the indicator ceases to prevail. Therefore, this approach, with suitable calibration, provides a direct measure of the concentration of the substance to be measured.

Briefly, and more specifically described, in this illustrative simple example, a sample to be analyzed for an analyte substrate is divided into portions and treated with identical quantities of reagents and catalyst for a "control" reaction of the analyte leading to a visible or otherwise detectable response, and with varying relative amounts of a catalyst which controls the rate of a second competing reaction that uses up the analyte substance to be measured. At low relative concentrations of the competing catalyst, sufficient analyte will remain to give a positive response in the control, indicator reaction. At higher relative concentrations of competing catalyst, concentration of analyte will drop below the level necessary for the indicator reaction to be detectable. The point of changeover from a positive to negative result provides an index to the concentration of analyte.

The basic concept (while illustrated above for the simplest case, where the analyte is a substrate for two competing catalysts) is capable of great versatility with respect to analyte. Such analytes include, in addition to enzyme substrates, enzymes, immunogens, and substances capable of specific affinity binding. Further illustration of additional embodiments is set forth hereinbelow.

Thus, in one aspect the invention relates to a method for determining the concentration of a desired analyte in a sample which method comprises contacting the sample or series of sample portions with pre-set amounts of the reaction components for a control reaction and variable relative amounts of catalyst for a competing reaction, where one of the control or competing reactions is also an indicator reaction.

The competition may be mediated by additional reagents specific for the analyte, such as antibodies, a specific affinity partner, or a reagent to effect formation of a secondary analyte. The competing reactions may themselves, however, confer the required specificity.

In instances where the analyte is an enzyme substrate, it is preferred that the control reaction be the indicator reaction; where the analyte is an enzyme, it is preferred that the competing reaction be indicating. Where the specificity is conferred by an immunological or specific affinity reaction, the indicator reaction may be either of the competing reactions.

In another aspect, the invention relates to test kits which contain the appropriate materials for carrying out the method of the invention, including, as needed, the reagents used, means for separating the solution to be analyzed into portions and of contacting the sample or these portions with the proper reagents, and support matrices which provide direct reading capability in pre-set pattern of reaction variation, as is described by the foregoing method of the invention.

BRIEF DESCRIPTION OF THE DRAWINGS

FIG. 3 diagrams the test matrix configuration for a "thermometer" analyzer.

FIG. 4 is a graphic representation of cholesterol determination results.

MODES OF CARRYING OUT THE INVENTION

A. Definitions

Figure 1:
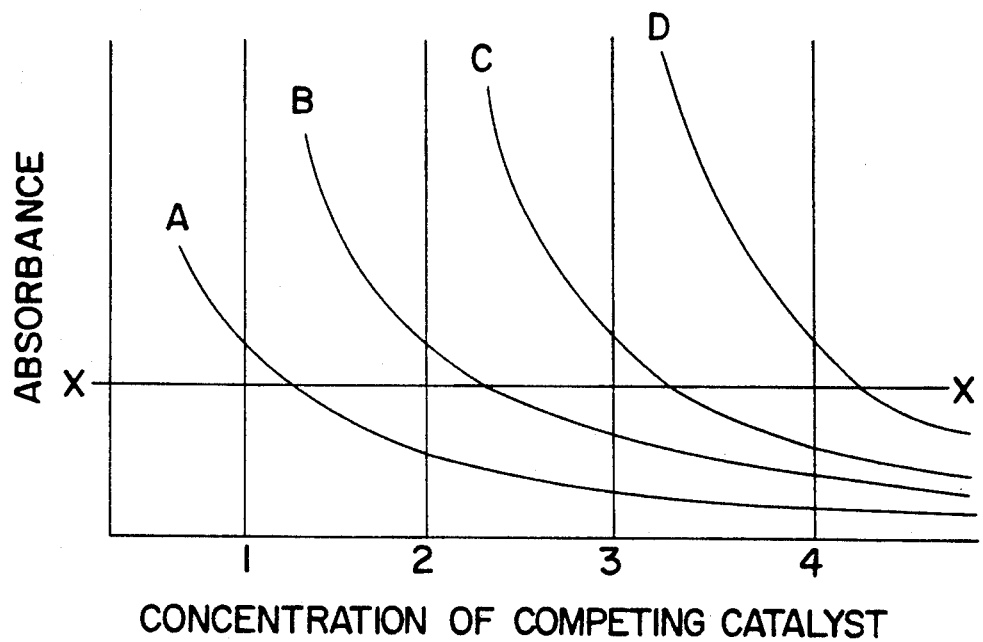
FIG. 1 shows the variation of absorbance with competing catalyst concentration for various analyte concentrations.

As used herein, "analyte" or "desired analyte" refers to the material whose concentration is to be measured. In the case of clinical tests, for example, such analytes might include an enzyme substrate, such as glucose, cholesterol, ammonia, urea, triglycerides, or amino acids; immunogenic substances, such as bacterial cell wall components or antibodies; other substances capable of specific affinity binding, such as biotin, or enzymes, such as phosphatase, glucose oxidase, urease, or any enzyme for which the substrate can be consumed by another, competing enzyme.

"Sample" refers to the material in which the concentration of the analyte is to be measured. Such samples may also be of almost infinite variety—from clinical samples such as blood and urine or derivatives thereof, to in vivo intracellular environments, to sewage treatment effluents and the like. As used herein, the term "sample" refers to a quantity of material, however prepared or found, which is to be assayed for the concentration of analyte present.

"Secondary analyte" refers to a material generated as a product of a reaction involving the desired analyte either as a substrate or as a catalyst. The specificity is controlled by the enzyme/substrate specificity of this preliminary reaction. Thus, for example, any analyte which can be reacted so as to form hydrogen peroxide can be quantitated by first effecting a hydrogen peroxide-producing conversion essentially to completeness and using the hydrogen peroxide as secondary analyte in a peroxidase/catalase competition. The specificity of the catalyst for the generation of hydrogen peroxide will limit the assay to the desired analyte. Either an enzyme, such as glucose oxidase, or a substrate, such as glucose could be added to permit the peroxide generation to take place, for assay of glucose, or glucose oxidase, respectively.

"Analyte conversion reaction" refers to this preliminary specific reaction which generates a secondary analyte to serve as the substrate for both the control and competing reactions.

The reactions described below may take place in more than one step, and "reaction" in the singular is intended to include both single step conversions and multiple step conversions, as will be clear from context.

"Reaction components" refers to catalyst(s) and/or such reactants as are not already present in the samples to be tested required to carry out the reaction in question.

"Control reaction" refers to an enzyme catalyzed reaction utilizing the same substrate as a competing reaction. The reaction components for the control reaction are added to the sample in pre-set amount.

"Competing reaction" refers to a reaction which utilizes as a substrate the same substrate as the control reaction and which is catalyzed by a "competing catalyst", which is added to the sample in variable amounts relative to the control.

In the most easily envisaged illustration, the control reaction components are added at constant, and the competing reaction at variable levels. However, clearly what is required is merely a progressive variation in the relative amounts of these components. Thus the control components concentration may also be varied, but are "pre-set" in the sense that the control reaction is used as the base against which the competing reaction is normalized.

(When referred to collectively, the control and competing reaction are sometimes designated, herein, "the competing reactions".)

"Indicator reaction" refers to a reaction which directly or indirectly depends on the concentration of the desired analyte or secondary analyte, and which produces a substance which is detectable. In its simplest embodiment, such product could be a material which is detectable by means of simply viewing its color.

For direct substrate analysis, the control reaction is also the indicator reaction. For indirect substrate analysis, the competing reaction is the indicator reaction. For enzyme analytes, the competing reaction is usually the indicator reaction simply for convenience. For immunoassays, or specific affinity assays, either the control or competing reaction can be indicating, but the control reaction is usually catalyzed by the enzyme conjugate provided in solution, and the competing reaction by that fixed to a solid support.

A "reagent specific for the analyte" refers to a reagent which will react only with the analyte among the components of the sample. The level of specificity depends, of course, on the nature of the contaminants in relation to the nature of the analyte.

The reagent specific for analyte may be provided by the competing reactions themselves—i.e., when the analyte is a substrate or enzyme for these competing reactions. It may, however, be provided as a supplement to these competing reaction components—i.e., when the competing reactions utilize a secondary analyte the reagent specific for analyte is a substrate or enzyme for the analyte conversion reaction; in immunoassays, the reagent specific for analyte is an antibody or derivative; in assays based on specific affinity, the reagent is a "specific affinity partner".

B. General Description of the Method

The method may be applied to a wide variety of analytes. In particular, the analyte may be 1) the substrate for both the control and competing reaction;

2) a substrate convertible to a substrate for both the control and competing reaction;

3) the catalyst for the control reaction;

4) the catalyst for the analyte conversion reaction;

5) an antigen reactive with a specific antibody;

6) a substance capable of specific affinity binding.

A detailed description of these embodiments appears in the paragraphs below.

The general concept which results in a self-contained quantification using a pair of competing catalysts can best be described in terms of a hypothetical set of results for one particular, non-limiting embodiment diagrammed in FIG. 1. In this illustration, the analyte is an enzyme substrate and the control reaction is the indicator reaction. The graphical representation in FIG. 1 is a plot of absorbance (y-axis) of a color product formed in an indicator reaction as a function of competing catalyst concentration (x-axis) for a series of four analyte concentrations A(lowest)-D(highest). Curves A, B, C and D represent the absorbance of the colored products obtained at varying levels of competing catalysts for this series A-D of successively increasing concentrations of analyte. The absorbance of the colored product for the lowest concentration of analyte, as shown in Curve A, is always, for a given concentration of competing catalyst, below that shown for the next lowest concentration of analyte for Curve B; which is in turn below that given for the higher concentration levels of analyte in C and D and so forth. The horizontal line at absorbance level X represents the level of detection possible with the naked eye—i.e., only those reactions which produce detectable products of absorbance higher than X can be seen. As shown on the graph, Curves A-D cross the visibility line at successively lower concentrations of competing catalysts. Thus, at concentration level 1 as shown in FIG. 1 of competing catalyst, even the analyte level represented by Curve A can be detected whereas at concentration level 4 of competing catalyst, even the analyte level represented by the highest concentration (D) falls above the X cutoff line. A tabulation of these results is shown in Table 1 below.

TABLE 1

| Analyte Concentration | Competing Catalyst Concentration | | | |
|---|---|---|---|---|
| | 1 | 2 | 3 | 4 |
| A | Y | N | N | N |
| B | Y | Y | N | N |
| C | Y | Y | Y | N |
| D | Y | Y | Y | Y |

Y = Yes (detectable)
N = No (not detectable)

Table 1 indicates that analyte levels A, B, C and D can be differentiated from each other entirely by their pattern of responses to varying levels of competing catalyst; thus level A give a visible response only at competing catalyst level 1, whereas level B gives a visible response at competing catalyst levels 1 and 2 but not at 3 and 4. Analyte at level D gives a visible response at all levels of competing catalyst concentration.

Thus, in carrying out this embodiment, the sample to be analyzed is divided into several portions each of which is then contacted with the necessary reagents and catalyst for the control/indicator reaction. Each portion is also contacted with the reagents and catalyst necessary for the competing reaction. By varying the amount of the competing catalyst relative to the control, the level of competition with the control/indicator reaction is also varied. Higher concentrations of analyte will be capable of carrying out the control/indicator reaction despite more effective depletion by the competing catalyst reaction, and the array of detectable versus undetectable reactions as a function of competing reaction catalyst or reactant will be characteristic of a particular analyte concentration.

In another embodiment, the competing catalyst can be used in competition for the same substrate as that used by an enzyme analyte which will be, therefore, the catalyst for the control reaction. Then, a fixed, limiting amount of this common substrate is added to the reaction mixture. Because it is unlikely that the enzyme analyte will catalyze a color-producing indicator reaction, a competing enzyme may conveniently be chosen which does so. Under these circumstances, the color will be less when the concentration of analyte is higher. Of course, if the control reaction is, coincidentally, useable as indicator, this may also be employed.

(While it is simpler in general that the control reaction be indicating, the competing reaction may also serve that function—i.e., the control (pre-set reaction component addition) reaction may simply be used as a conterfoil for a competing/indicator reaction).

In another variation, the analyte to be measured generates a "secondary analyte" by virtue of a suitable analyte-specific reaction. This secondary analyte replaces the analyte to be measured as the substrate for the competing control and competing reactions. Thus, in this variation, the sample to be analyzed is provided with, in addition to the components added as described above, reaction components for the analyte conversion. This confers specificity on the test, as well as providing the secondary analyte which forms the substrate for the competing reactions. By virtue of this variation, a standard competition pattern can be applied to a number of desired analytes as long as these analytes generate the same secondary analyte.

When the analyte is, itself, an enzyme, a constant amount of substrate convertible to a secondary analyte is used. Thus, the secondary analyte is a product of the added substrate, and is in a concentration proportional to the enzyme analyte concentration. The remainder of the method is, then analogous to that described for analytes which are substrates.

For example, $H_2O_2$ can be detected by competition between peroxidase and catalase controlled reactions as further described in the Examples below. A number of primary analytes can be used to generate the peroxide as a secondary analyte—e.g., glucose (glucose oxidase), cholesterol (cholesterol oxidase) and creatinine (creatinine amidino-hydrase and sarcosine oxidase); see Forsati, P. et al, *Clin Chem,* 19:1494 (1983).

It is not necessary that the analyte be either an enzyme or the substrate for a specific enzyme reaction. It is also possible to use the general method of the invention to quantitate the amount of any material which is capable of generating antibodies, or of a substance capable of specific affinity binding, by providing a support with varying amounts of competing reaction catalyst in a prescribed geometric pattern disposed on the surface among a set concentration of antibody or other affinity binding partner specific for the analyte. The catalyst for the control reaction will be supplied in pre-set amount by contacting the support with a solution containing control catalyst simultaneous with or subsequent to contacting the support with the sample. The antigen-antibody or affinity interaction regulates the level of control enzyme supplied to all locations on the support as a function of the level of analyte in solution. The protocol can be arranged in a variety of ways, as outlined in detail below, but the fundamental concept is to use the antigen/antibody specificity or affinity binding specificity to control the amount of control enzyme catalyst reaching the varying levels of competing enzyme catalyst. Depending on the design of the specific embodiment, and whether the control or competing reaction is indicating, the test can be designed so that the indicator reaction level is either directly or inversely proportional to the analyte concentration in the sample.

C. Assay Configurations

In one preferred assay design related to analysis for enzymes or their substrates, separate containers are provided with equal amounts of a solution containing all of the necessary reactants and catalyst (or substrate) for effecting the control reaction and with quantities of solution containing reactants and varying amounts of catalyst necessary for effecting the competing reaction. Dried reagents and catalysts which can be reconstituted with water may also be used. In either case, the reaction is essentially "wet" chemistry and only the mode of reagent supply differs. To this series of containers, which now contains fixed quantities of control reaction components, and variable amounts of competing reaction components is added equal quantities of the sample to be assessed. After the requisite amount of time to permit the reactions to go to completion, the containers are observed to ascertain whether or not detectable product is in fact visible. By comparing the pattern of visibility/invisibility as a function of competing catalyst concentration to that obtained from a previously determined set of standard analyte concentrations, the analyte concentration of the test sample is then determined.

The times, temperatures, pH and other conditions operable and preferred for any particular embodiment will, of course, depend on the specific nature of the reagents and the catalyst used. In general, for reactions useful in clinical applications room temperature to around 37° C. at the pH optimum of the enzyme in question, usually around neutrality, and for reaction times appropriate to the level of substrate being tested are used. Preferably, the conditions of the reaction in terms of concentrations of materials are optimized so that dependable and reproducible results can be obtained within a period of about 10 minutes over about a 10-fold concentration range of analyte.

In a still more preferred design, a suitable support matrix, such as, for example, filter paper, silica gel plates, or other absorbent is impregnated with a solution containing the reagents and catalyst (or substrate) for the control reaction distributed evenly over and throughout the support. This support is then subdivided into a series of test regions, preferably distributed about a central point but in any suitable configuration for ease of sample handling and reading. To each testing region is added a specific reactive level, differing sequentially from region to region of components for effecting the competing reaction. Such a pattern could be obtained, for example, by blotting the support against a suitable template containing the various concentration levels of these materials in a patterned array of suitable containers. The resulting test sheet will thus be impregnated with a corresponding array of test positions which offer varying levels of competition for the analyte. All of these operations can be performed at a manufacturer's facility, and the prepared matrix supplied to the end user.

Such systems are basically "dry" chemistry—i.e., the reactions take place without the use of solvent to reconstitute the components of the systems. The technology associated with preparing such systems is now well-established and fairly sophisticated. A number of such systems for qualitative and quantitative analysis are now available, from the familiar and seminal litmus paper developed in the 19th century, to the multi-layered and complex systems employed in instant photography. A number of dry chemistry systems based, on, for example, color comparisons are also now available, such as reagent test strips for blood glucose or urine sugar content for use by diabetics. See, for example, Akai, T., et al, *Clinical Chemistry,* 29:1825 (1983)) (urea nitrogen in saliva); Dappen, G. M., et al, Ibid, 28:1159 (1982) (cholesterol in serum). Procedures for producing such dry chemistry support systems are will known in the art (Walter, B., *Anal Chem,* 55:498A (1983)).

The sample to be analyzed is then permitted to contact the various testing regions and the regions are scored according to whether or not visible product is noted. From the resulting pattern of positive and negative results, the concentration of analyte in the test sample can be assessed. Exact quantitative assignment of a numerical value for the concentration can be achieved by comparison with corresponding results from a series of appropriately diluted standards containing analytes in similar samples, i.e., precalibration with known samples is required.

Of course, as above, the incubation time, temperature and pH conditions for the method carried out on a solid matrix support will be dependent on the specific components of the system.

Figure 2:
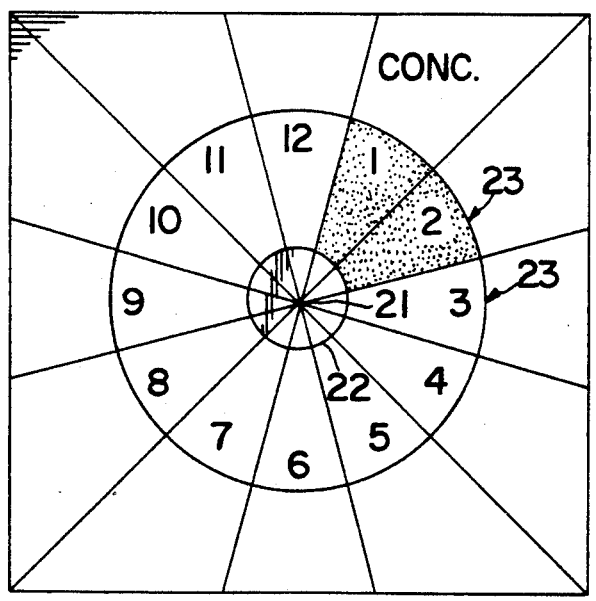
FIG. 2 diagrams the test matrix configuration for a "clock" analyzer.

One arrangement is that depicted in FIG. 2. The test matrix is divided into a series of arc segments, each of which contains pre-set amounts of control/indicator reaction components. As the series proceeds clockwise from 12 o'clock, each segment has a progressively greater relative amount of competing enzyme (along with additional reagents for the competing reaction if necessary). The sample is applied at the center 21, and allowed to diffuse through the matrix. If the sample contains interfering materials, e.g., red blood cells in a whole blood sample, it is desirable to interpose a semipermeable membrane 22 in a 360° arc such that the supernatant diffuses past the membrane and into the test areas 23. Depending on the concentration of analyte in the sample, segments will exhibit observable color through to later and later positions on the clock. Thus by reading the "time" at which the color stops, the range of amounts of analyte can be ascertained. A sample showing color up to only 2 o'clock is much less concentrated in analyte than one which shows color up to 11 o'clock.

A more preferred configuration is the "thermometer" shown in FIG. 3. The support has increasing concentrations of competing reaction components in the segments as the test segments, 31, are arranged from right to left. If configured for analysis of a secondary analyte, equal amounts of specific analyte reaction catalyst may also be included in each segment (or subsequently added); if for immunoassay or specific affinity, specific antibodies or affinity partners are supported on the matrix (see ʳD below). Samples or aliquots of the material to be tested are placed on each spot, or the support is dipped into the sample, and the ranges represented by color progression to a particular location denoted alongside (32). The assay may be designed so that the more concentrated the sample, the farther to the left (as shown in FIG. 3) will extend the color bar.

Both "clock" and "thermometer" configurations are also useful for use of a convenient display of qualitative results in a series of different tests. The matrix could contain in one segment the reagents for glucose assay, in another for ammonia, in another for urea, etc.

D. Immunoassays and Specific Affinity Binding Assay

Modifications which take advantage of the specific antigen/antibody reaction of an analyte with immunoglobulins raised in response to its injection into a subject mammal or which utilize specific affinity binding of the analyte to a partner compound all involve the use of solid supports and a patterned distribution of competing enzyme attached to the solid support.

The pattern of distribution may be similar to that set forth above in connection with the assay system as applied to substrates or enzymes—i.e., in the form of a "thermometer" or a "clock". Suitable solid supports include those conventionally used in immunoassays, typically agar, polystyrene, ion exchange resins, glass, agarose, dextran and derivatives. The antibodies or affinity partner molecules are adsorbed or conjugated covalently to the support using means known in the art. Similarly, the enzyme for the competing reaction is distributed over the surface and attached either by adsorption or covalent linking in a pattern of increasing density of enzyme such as through the a tube analogous to that containing the mercury in a thermometer of a thermometer or through the progression of hours in a clock. Adsorption or covalent attachment of proteins and other materials to supports is well understood, and detailed protocols are available which are applicable to both competing enzyme and reagent specific for analyte. See *Methods if Enzymol* Vol XLIV (1976) "Immobilized Enzymes" (Academic Press) Mosbach, K., Ed.

The support is then treated with a protocol which includes the solution to be analyzed and the reaction components for the control reaction. The level of control enzyme is regulated by the quantity of analyte in the solution, either because, for example, the control enzyme is bound to the analyte antigen in competition with the analyte concentration in the sample, or because it is bound to additional antibody, which will then bind only where antigen is present, or, by virtue of competition for space on the support between the antibodies against analyte and antibodies directed against, but not inactivating, the control reaction enzyme. Similarly, when specific affinity binding is used, the control enzyme may be conjugated to competing analyte, or to binding partner capable of attaching to analyte bound to the support. The details of such protocols are set forth in F below.

E. Kits and Supports

The materials usable in the methods of the invention can be supplied in convenient form as a kit or as a test matrix. Thus, the scope of the invention also includes such package configurations which offer the convenience of providing an organized system for carrying out the method of the invention. Enzymes or other catalysts and reactants usable in the methods of the invention can be supplied in solution or dried form and may be placed in a marketable kit in reaction vessels or as a diagrammed matrix containing the appropriate testing regions, depending on the nature of the assay. A particularly preferred embodiment for assays in which the analyte is an enzyme or substrate comprises a series of reaction vials containing dried reagents for the control, and, if appropriate, specific analyte reactions, in pre-set amounts for each vessel, and the reactants and catalysts for the competing reaction in varying relative amounts. For use, the vials can simply be activated by adding an appropriate amount of water, or of the sample solution directly. A suitable series of containers can be provided by ordinary vials, or by microtiter plates commonly in use in serial dilution based reactions in microbiology.

The solid support matrix alternative has been described in some detail above and is applicable to analysis based on the specific immunological or affinity binding response of the analyte. For enzyme or substrate analysis, some reagents may be fixed to the support, and others added subsequently to the support. For immunological or specific binding assays, the specific antibodies or specific affinity partner and competing catalyst must be previously immobilized to the support, and the control components added separately.

F. Exemplary Protocols

The components of the test kits would, thus, in general, comprise suitable reagents and catalysts for the control, competing, and, if applicable, reagents for an analyte conversion reaction, antigen/antibody reaction or affinity binding reaction. Either the control or competing reaction, as a suitable indicator reaction may be, for example, oxidation of hydrogen peroxide using peroxidase and a dye-generating reducing agent, oxidation of glucose with glucose oxidase coupled to a peroxidase dye producing reaction, or a reaction of any analyte catalyzed by a specific enzyme which generates $H^+$ in the presence of a pH indicator. Dyes useable in the peroxidase catalyzed reaction in addition to those listed below include 2,2-azino-di-(3-ethylbenzthiazoline sulfonate) (ABTS ®), tetramethylbenzidine, and 4-chloro-1-naphthol.

Exemplary of schemes which take advantage of such reactions are as follows: (the systems in a-e are for determination of substrate type analytes; f-h, for determination of enzyme analytes, and the protocols in i for antigen/antibody and specific affinity binding reactions.

a) Glucose Determination

Method 1: *Control/Indicator Reaction $$\text{Glucose} + O_2 \xrightarrow{\text{Glucose Oxidase}} \text{Gluconolactone} + H_2O_2;$$

$$H_2O_2 + \text{4-Aminoantipyrene} +$$

$$\text{p-Hydroxybenzoate} \xrightarrow{\text{Peroxidase}}$$

$$\text{Quinoneimine Dye} + H_2O$$

*Competing reaction:

$$\text{Glucose} + \text{ATP} \xrightarrow{\text{Hexokinase}} \text{Glucose 6-phosphate} + \text{ADP}$$

Method 2: *Control/Indicator Reaction $$\text{Glucose} + \text{ATP} \xrightarrow{\text{Hexokinase}} \text{Glucose-6-phosphate} + \text{ADP}$$

$$\text{Glucose-6-Phosphate} + \text{NAD} \xrightarrow{\text{Glucose-6-phosphate dehydrogenase}}$$

$$\text{NADH}_2 + \text{Phosphogluconate}$$

$$\text{NADH}_2 + \text{Tetrazolium salt} \xrightarrow{\text{Diaphorase}}$$

$$\text{NAD} + \text{Formazan (colored)}$$

*Competing Reaction:

$$\text{Glucose} + O_2 \xrightarrow{\text{Glucose Oxidase}} \text{Gluconolactone} + H_2O_2$$

Method 3: *Specific Analyte Reaction $$\text{Glucose} + O_2 \xrightarrow{\text{Glucose Oxidase}} \text{Gluconolactone} + H_2O_2$$

*Control/Indicator Reaction
$H_2O_2 + $ 4-Aminoantipyrene +

$$\text{p-Hydroxybenzoate} \xrightarrow{\text{Peroxidase}}$$

$$\text{Quinoneimine Dye} + H_2O$$

*Competing Reaction:

$$2H_2O_2 \xrightarrow{\text{Catalase}} 2H_2O + O_2$$

Method 4: *Specific Analyte Reaction $$\text{Glucose} + \text{ATP} \xrightarrow{\text{hexokinase}} \text{Glucose-6-phosphate} + \text{ADP}$$

$$\text{Glucose-6-phosphate} + \text{NAD} \xrightarrow{\text{Glucose-6-phosphate dehydrogenase}}$$

$$\text{NADH}_2 + \text{Phosphogluconate}$$

*Control/Indicator Reaction $$\text{NADH}_2 + \text{Tetrazolium salt} \xrightarrow{\text{Diaphorase}} \text{NAD} + \text{Fomazan}$$

*Competing Reaction:

$$\text{Pyruvate} + \text{NADH}_2 \xrightarrow{\text{Lactate Dehydrogenase}} \text{Lactate} + \text{NAD}$$

b) Cholesterol Determination
*Specific Analyte Reaction $$\text{Cholesterol} + O_2 \xrightarrow{\text{cholesterol Oxidase}} \text{cholesten-3-one} + H_2O_2$$

*Control/Indicator Reaction
$2H_2O_2 + $ 4-Aminoantipyrene +

$$\text{p-Hydroxybenzoate} \xrightarrow{\text{Peroxidase}}$$

$$4H_2O_2 + \text{Quinoneimine dye}$$

*Competing Reaction $$2H_2O_2 \xrightarrow{\text{Catalase}} 2H_2O$$

c) Uric Acid Determination
*Specific Analyte Reaction $$\text{Uric Acid} + O_2 \xrightarrow{\text{Uricase}} H_2O_2 + \text{Alantoin}$$

*Control/Indicator Reaction
$H_2O_2 + $ 4-Aminoantipyrene +

$$\text{p-Hydroxybenzoate} \xrightarrow{\text{Peroxidase}}$$

$$4H_2O + \text{Quinoneimine Dye}$$

*Competing Reaction:

$$2H_2O_2 \xrightarrow{\text{Catalase}} 2H_2O + O_2$$

d) Triglyceride Determination
Method 1: *Specific Analyte Reaction $$\text{Triglycerides} + H_2O \xrightarrow{\text{Lipase (EC 3.1.13)}} \text{Glycerol} + \text{Free fatty acids}$$

$$\text{Glycerol} + \text{ATP} \xrightarrow{\text{Lipase (EC 2.71.30)}}$$

$$\text{ADP} + \text{L-}\alpha\text{-Glycerol-phosphate}$$

$$\text{L-}\alpha\text{-Glycerol-phosphate} + O_2 \xrightarrow{\text{L-}\alpha\text{-glycerol-phosphate oxidase}}$$

$$H_2O_2 + \text{Dihydroxyacetone-phosphate}$$

*Control/Indicator Reaction
$H_2O_2 + $ 4-Aminoantipyrene +

$$\text{p-hydroxybenzoate} \xrightarrow{\text{Peroxidase (EC 1.11.1.7)}}$$

$$2H_2O + \text{Quinoneimine Dye}$$

*Competing Reaction:

$$2H_2O_2 \xrightarrow{\text{Catalase}} 2H_2O + O_2$$

e) Creatinine Determination
*Specific Analyte Reaction $$\text{Creatinine} + H_2O \xrightarrow{\text{Creatinine amidinohydrolase (EC 3.5.3.3)}}$$

$$\text{Urea} + \text{Sarcosine}$$

-continued

Sarcosine + H$_2$O + O$_2$ $\xrightarrow{\text{(EC 1.5.3.1)}}$ Glycine + Formaldehyde + H$_2$O$_2$

*Control/Indicator Reaction

H$_2$O$_2$ + 4-Aminoantipyrene + p-Hydrobenzoate $\xrightarrow{\text{Peroxidase}}$ Quinoneimine dye + 4H$_2$O

*Competing Reaction:

2H$_2$O$_2$ $\xrightarrow{\text{Catalase}}$ 2H$_2$O + O$_2$ f) Lactate Dehydrogenase (LDH) Determination

*Control Reaction

Pyruvate + NADH$_2$ $\xrightarrow{\text{LDH}}$ L-lactate + NAD
(with NADH$_2$ limiting)

*Competing/Indicator Reaction:

NADH$_2$ + Tetrazolium salt $\xrightarrow{\text{Diaphorase}}$ NAD + Formazan g) Determination of Alanine Aminotransferase (ALT)

Control Reaction

L-glutamate + Pyruvate $\xrightarrow{\text{ALT}}$ L-Alanine + α-ketoglutarate
(with glutamate limiting)

*Competing/Indicator Reaction:

L-glutamate + NAD$^+$ + H$_2$O $\xrightarrow[\text{dehydrogenase}]{\text{Glutamate}}$ α-ketoglutarate + NH$_3$ + NADH$_2$ NADH$_2$ + Tetrazolium salt $\xrightarrow{\text{Diaphorase}}$ NAD + Formazan h) Aspartate Aminotransferase (AST) Determination

*Control Reaction

L-glutamate + Oxaloacetate $\xrightarrow{\text{AST}}$ L-aspartate + α-ketoglutarate
(with glutamate limiting)

*Competing/Indicator Reaction:

L-glutamate + NAD$^+$ + H$_2$O $\xrightarrow[\text{Dehydrogenase}]{\text{Glutamate}}$ 2-oxoglutarate + NH$_3$ + NADH$_2$ NADH$_2$ + Tetrazolium salt $\xrightarrow{\text{Diaphorase}}$ NAD + Formazan The analyte for the method of the present invention need not be, itself, either a substrate for enzymic activity or an enzyme. It need merely be a material which possesses affinity binding characteristics or against which antibodies can be made. In the design of this aspect of the invention, a solid support is provided to which is bound a pre-set amount of antibody specific against the analyte or affinity partner and, interspersed with bound antibody or affinity partner, an amount of enzyme for the competing reaction, which varies with location on the solid support. In an ideal, and most simply understood embodiment, an incremental or continuous one-dimensional variation in competing enzyme bound concentration is arrayed on the support, in a manner similar to the "thermometer" shown in FIG. 3. The sample to be analyzed and the remaining reagents are added to the solid support, most easily by simply dipping the support into the sample to be analyzed, and/or solution supplying the reagents for the control reaction. An arbitrary substrate for control and competing reactions can be used; as shown in the foregoing examples, hydrogen peroxide, glucose, NAD, NADH$_2$, glutamate, pyruvate, and a variety of other substrates find pairs of enzymes which can compete for their reactivity. These substrates are supplied in the reaction mixture, independent of the nature of the analyte, and are thus applied, in predetermined amount, over the surface of the support.

This embodiment of the invention is responsive to the quantity of analyte in the sample because the amount of analyte available for binding to the solid phase antibody or affinity partner regulates the amount of control enzyme which in fact competes with the bound competing enzyme. Either the control or competing reaction may be indicating, and the response may be either directly or inversely proportional to the amount of analyte.

These concepts are, perhaps, best understood by specific illustration. For illustrative purposes only, the hydrogen peroxide/peroxidase/catalase system will be used. This is the same paired system used above in connection with a plurality of determinations based on conversion to a secondary analyte. In this system, peroxidase catalyzes an indicator reaction wherein, for example, hydrogen peroxide is reacted with aminoantipyrene and p-hydroxybenzoate to generate water and quinoneimine dye. Catalase simply affects the rate of decomposition of hydrogen peroxide into water and oxygen, and produces no color. Either the peroxidase or the catalase may be bound to the support in varying amounts, interspersed with a pre-set concentration of bound antibody or affinity partner corresponding to the desired analyte. The coated support is then treated with the sample to be analyzed, with specifically bound enzyme for the control reaction, and with a developing solution containing substrate for the control and competing reactions.

i) The following outlines of protocols are intended to be illustrative of sequences which employ the basic elements of the method of the invention—i.e., a self-contained self-quantitating measure of analyte concentration which employs concentrations of control reaction components and variable relative quantities of competing reaction components.

In all the following examples the solid support, having affinity partners or antibodies specific to the analyte arrayed over its surface, is provided a linear gradient of linked enzyme for the competing reaction. The reagent specific to analyte and the competing enzyme can be, if desired, simultaneously immobilized using techniques set forth by, for example, Chibata, I. (Ed.) "Immobilized Enzymes Research Development", Halsted Press (1978) N.Y., or Jacoby, W. B., et al, *Meth Eng* XXXIV, (1974) "Affinity Techniques, Enzyme Purification; part B", Academic Press, N.Y. The support is made up in segments, so that the gradient of competing enzyme can be prepared by assembling segments contacted with different enzyme concentrations.

In one protocol the solid support is then exposed to a sample containing analyte, which analyte then occupies some of the antibody binding or affinity partner sites. After washing, the solid, now containing some bound analyte, is exposed to solution containing the control reaction enzyme covalently linked to the analyte molecules. Methods for conjugating enzymes to carrier molecules are well understood. See, for example, Wilson, M. B., et al, "Immunofluorescense and Related Staining Techniques", pp 215-224, Elsevier Press, Holland, N.Y. (1978). At least some of the remaining antibodies or affinity partners are available to be bound to analyte conjugated to the control reaction enzyme. Of course, the amount of conjugated control reaction enzyme bound will be less, the higher the analyte concentration in the sample. The solid support is then treated with a developing solution containing substrate and reaction components for the two reactions in competition, in this case hydrogen peroxide, aminoantipyrene, and hydroxybenzoate in suitable buffer. In those regions of the gradient where the competing enzyme concentration is highest, more control enzyme will be required to block out the competing reaction. At high concentrations of analyte in the sample, the point in the competing enzyme gradient where the competing reaction begins to be dominated by the control reaction will be at lower concentration of competing enzyme than where the level of analyte in the sample is low. Thus, for the case where the competing reaction is also the indicator reaction (peroxidase), higher concentrations of analyte will result in a larger portion of the gradient showing the colored quinoneimine dye-product of the indicator. It does not matter in this protocol whether the support is treated with sample and control enzyme sequentially, or simultaneously.

Illustrative analytes for which this protocol is applicable include biotin and such immunogens as viral capsid proteins. For biotin, the reagent specific for analyte will be avidin, for capsid proteins, antibodies raised against them. The biotin containing sample, for example, also containing biotin-conjugated horseradish peroxidase (HRP) is contacted with a support containing immobilized avidin and a gradient immobilized catalase. After washing, a developing solution containing $H_2O_2$ and the color generating reagents is added.

In a modification of this protocol, the control enzyme, rather than being bound to competing analyte, is conjugated instead to an antibody or affinity partner which reacts with a different site on the analyte antigen than does the antibody bound to the support. Thus, the more analyte molecule which are bound to the support, the higher the concentration of control enzyme. In order to make the indicator color directly proportional to the amount of analyte, the control reaction should be the indicator reaction (peroxidase) in this protocol, and the competing reaction that catalyzed by catalase.

For example, biotin would be measured by contacting the sample with a support containing immobilized avidin and catalase, as above, but would then be washed and treated with HRP conjugated to avidin. Or human chorionic gonadotropin (hcG) could be measured by contact with a support having a first anti-hcG along with a catalase gradient, followed by washing and treating with HRP bound to a second anti-hcG.

In other embodiments, the analyte may be used to provide blockage of additional antibody or affinity partner sites on the support directed specifically against the control reaction enzyme. This may be accomplished directly if the analyte is a bulky molecule which has sufficient size, itself, to block substantial areas of the support. If it is not sufficiently large, a conjugated protein, such as BSA, which provides this bulk, may be used when control analyte is applied. In either case, a support is prepared containing the enzyme catalyzing the competing reaction in linear gradient along with a mixture one two specific reagents or specific for the analyte and the other for the control enzyme. This support is then treated with the sample containing either the bulky analyte itself, or the analyte in competition with analyte molecules made bulky with, for example, BSA. The solid support is then washed and treated with the control reaction enzyme and then with substrate. The color produced will be dependent upon the amount of control reaction enzyme which is bound, which will be less in the case of high concentrations of bulky analyte, or more in high concentrations of analyte placed into competition with analyte bound to BSA. Whether the color produced is a direct or inverse measure of the analyte concentration in either case will depend on whether the indicator reaction is chosen to be the control or the competing reaction.

These various protocols are illustrated for the general case in FIG. 5. The figure is drawn in terms of antigen/antibody interactions; however precisely the same protocols may be used for specific affinity binding partners, except that instead of antibody a specific affinity binding partner to the analyte is used. In all cases the enzyme ($E_1$) which is bound to the support is disposed as a gradient made up of segments containing increasing densities of $E_1$.

Figure 5A:
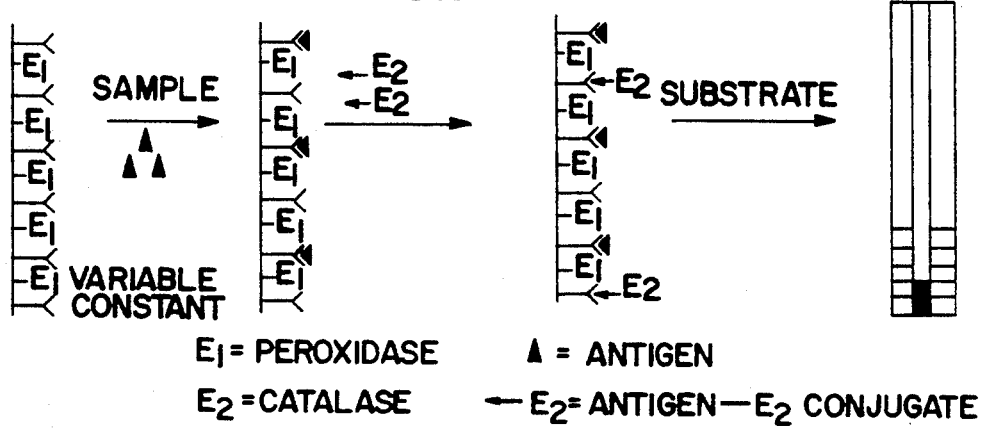
FIG. 5 illustrates, diagrammatically, the use of the invention for immunological or specific affinity based assays.
Figure 5B:
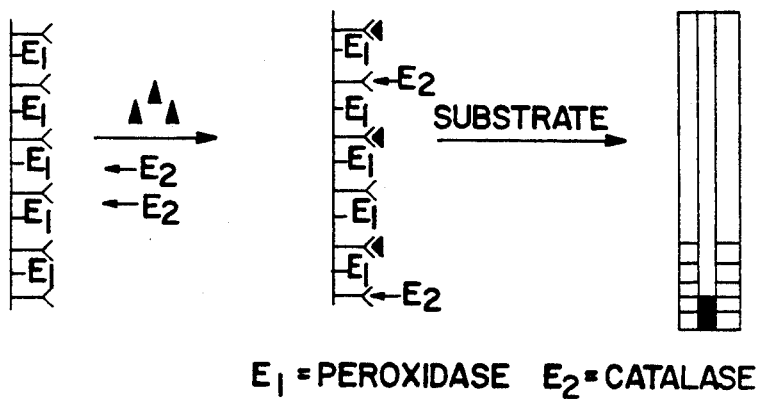

FIGS. 5a and 5b illustrate the method based on competition for bound antibody sites between the analyte in the sample, and control enzyme conjugated to analyte molecules.

Figure 5C:
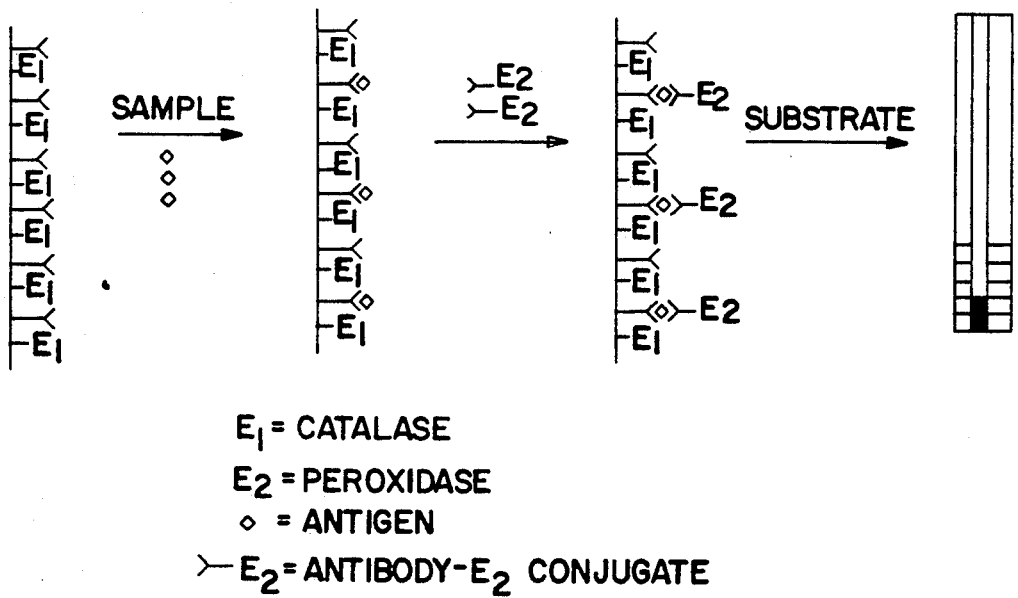

FIG. 5c shows a procedure based on the ability of control enzyme bound to anti-analyte antibodies to be bound to the support at locations occupied by the analyte.

FIGS. 5d and 5e illustrate the method whereby bound analyte creates steric interference with respect to binding of the control enzyme.

G. Examples

The following examples are meant to illustrate the invention, and not to limit it. Because of the wide variety and large number of reactant/catalyst combinations which can be used for each of the control, competing, or specific analyte reactions, the invention is best illustrated by use of specific examples using specified embodiments of these reactants and catalysts. Accordingly, the examples below provide methods for analyzing for glucose or for cholesterol using a number or reactant catalyst compositions which are readily available in the art. However, depending on the nature of the sample to be analyzed, entirely different embodiments of such reagents and enzymes will be possible and, indeed, necessary. The scope of the method is almost universal when immunological or specific affinity binding based assays are included.

G.1. Determination of Parameters to Provide A Glucose Test

In each of the examples below, the concentration of glucose tested is in the range of 0.01-0.3 $\mu$moles per ml (i.e., about 1.8-54 $\mu$g per ml). The assays are run at a reaction volume of 1.01 ml.

G.1.a. Glucose Oxidase as Competing Catalyst

To determine suitable concentration ranges for the competing catalyst and substrate concentration, the method of the invention was employed using as indicator reaction the conversion of glucose to glucose-6-phosphate in the presence of hexokinase, and the subsequent conversion of the glucose-6-phosphate to the corresponding carboxylic acid with the stoichiometric conversion of oxidized NAD+ to NADH. NADH id detectable by absorbance at 340 nm, thus, the level of absorbance at 340 nm can be used as an index of visibility. Further, the conversion of NAD+ to NADH can be utilized as a visible marker by supplying, in addition, a leuco dye and diaphorase. Thus, the reaction:

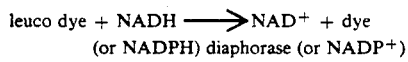

$$\text{leuco dye} + \text{NADH} \xrightarrow{\text{(or NADPH) diaphorase}} \text{NAD}^+ + \text{dye} \text{ (or NADP}^+)$$

results in an observable color change proportional to the NADH generated (and to what is measured in this Example as 340 absorbance).

The competing reaction was the direct oxidation of glucose using, as competing catalyst, glucose oxidase. The results were determined at both ambient temperature and at 37° C.

each reaction vessel contained in 1.01 ml total sample volume,
1.5 units per ml hexokinase
0.77 μmole/ml ATP
1.9 units per ml glucose-6-phosphate dehydrogenase
0.91 μmole/ml NAD
The mixture was buffered at pH 7.6.

These quantities represent an excess of reagents and sufficient catalyst to consume completely the levels of glucose supplied in the indicator reaction. The glucose is diluted 1:100 in the sample volume, so the concentrations are 0.01 of those shown in Tables 2-4. For each sample of glucose to be tested, a series of five vessels was used containing respectively 0, 62.5, 125, 250, and 500 units per ml of glucose oxidase.

The foregoing materials for the indicator reaction were supplied by reconstituting the Worthington StatzymeM Glucose Kit, catalog #27536. Glucose oxidase was obtained from Cal Biochem Boehringer and had a specific activity of 155 units per mg.

Table 2a and 2b show the results at ambient temperature, and at 37° for a series of six glucose samples of various concentrations.

TABLE 2a

| Glucose Concentration (mg/ml) | $OD_{340}$ after 4 minutes at room temperature |  |  |  |  |
|---|---|---|---|---|---|
| | Glucose oxidase Conc. (U/ml) | | | | |
| | 0 | 62.5 | 125 | 250 | 500 |
| 0.31 | .107 | .080 | .085 | .074 | .064 |
| 0.62 | .217 | .134 | .170 | .145 | .122 |
| 1.25 | .418 | .320 | .291 | .280 | .237 |
| 2.5 | .861 | .594 | .621 | .530 | .424 |
| 5.0 | 1.523 | 1.226 | 1.149 | 1.002 | .815 |

TABLE 2b

| Glucose Concentration (mg/ml) | $OD_{340}$ after 10 minutes at 37° C. |  |  |  |  |
|---|---|---|---|---|---|
| | Glucose oxidase Conc. (U/ml) | | | | |
| | 0 | 62.5 | 125 | 250 | 500 |
| 0.31 | .108 | .081 | .086 | .073 | .062 |
| 0.62 | .220 | .178 | .175 | .137 | .119 |
| 1.25 | .383 | .314 | .294 | .267 | .236 |
| 2.5 | .710 | .617 | .647 | .510 | .432 |
| 5.0 | 1.734 | 1.139 | 1.168 | .946 | .710 |

These results indicate that in order to find a suitable cutoff visibility line, higher concentrations of glucose oxidase should be used, since only at very high concentrations of glucose does the oxidase appear to compete effectively with the indicator reaction. However, it is clear that concentration of glucose oxidase does affect the "visibility" of the indicator reaction, and that the amount of "visibility" is proportional to the level of glucose in the sample.

G.1.b. Hexokinase As Competing Catalyst

A similar determination was conducted reversing the roles of the indicator and competing reactions. The indicator reaction was supplied using Worthington StratezymM catalog #27632 at concentrations which provide in each vessel sufficient catalyst and reactants to convert a suitable colorless dye precursor into visible dye. The dye is formed due to hydrogen peroxide generated by reaction of glucose with glucose oxidase. Thus, each vessel contains:
6.9 units per ml glucose oxidase,
0.5 μmole/ml 4-aminoantipyrine,
21.8 μmole/ml sodium-p-hydroxybenzoate,
0.5 units per ml peroxidase,
and buffer to maintain the pH at 7.0.

Each series of vessels for a given glucose sample contains the following amounts of hexokinase and ATP, respectively per ml, 0 IU, 0 μmoles; 32.4 IU, 1-μmoles, 64.8 IU, 20 μmoles; 129.6 IU, 40 μmoles. The same sample levels of glucose were used as in ʳ G.1.a above for the series set, i.e., the concentrations in Table 2 are diluted 1:100 in the test solution. The results were read at 500 nm (the absorbance maximum of the indicator reaction product) after 10 minutes at 37° C., and are shown in Table 3.

TABLE 3

| Glucose Concentration mg/ml | Concentration of Hexokinase IU/ml |  |  |  |
|---|---|---|---|---|
| | 0 | 32.4 | 64.8 | 129.6 |
| 0.31 | 0.093 | 0.079 | 0.053 | 0.027 |
| 0.62 | 0.195 | 0.169 | 0.104 | 0.061 |
| 1.25 | 0.392 | 0.352 | 0.244 | 0.126 |
| 2.5 | 0.797 | 0.729 | 0.434 | 0.259 |
| 5.0 | 1.303 | 1.250 | 1.089 | 0.577 |

The results indicate that if a level of visibility at OD=0.1 is assumed, glucose levels in the range of 0.017-0.069 μmole/ml can be ascertained, using this embodiment. Of course, any sample of greater concentration can be used with proper dilution.

G.2. Assay for Glucose Using a Specific Analyte Reaction

Similar ranges of glucose concentrations were tested using a specific analyte reaction to produce hydrogen peroxide at the expense of glucose permitting an indicator reaction based on the decomposition of hydrogen peroxide catalyzed by peroxidase and simultaneous formation of a dye as set forth in Paragraph G.1b. The competing reaction is the decomposition of hydrogen peroxide using variable levels of catalase.

To each reaction vessel was added a sufficient quantity of glucose oxidase and suitable peroxidase components as supplied by Worthington StatzymeM catalog #27632 as set forth in G.1.b. above to provide:
13.8 units per ml glucose oxidase,
1.0 μmole/ml 4-aminoantipyrene,
43.6 μmole/ml sodium p-hydroxybenzoate, and
1 unit per ml peroxidase.

Each series of vessels contained catalase in concentrations of 0, 640, 1280, 2560, and 5120 units per ml. The concentration of glucose provided to each series of vessels was as set forth in ᶜ G.1. above, and the reaction was carried out at 37° C. and read after 10 minutes at 500 nm, as above. The results are shown in Table 4 (again, the concentration is prior to the 100:1 dilution of the assay).

TABLE 4a

| Glucose Concentration | Catalase (U/ml) | | | |
| --- | --- | --- | --- | --- |
| mg/ml | 640 | 1280 | 2560 | 5120 |
| 0.31 | 0.047 | 0.034 | 0.025 | 0.007 |
| 0.62 | 0.105 | 0.073 | 0.045 | 0.018 |
| 1.25 | 0.217 | 0.150 | 0.088 | 0.043 |
| 2.5 | 0.437 | 0.297 | 0.177 | 0.088 |
| 5.0 | 0.860 | 0.601 | 0.352 | 0.185 |

TABLE 4b

| Glucose Concentration | Catalase (U/ml) | | | |
| --- | --- | --- | --- | --- |
| mg/ml | 640 | 1280 | 2560 | 5120 |
| 0.31 | N | N | N | N |
| 0.62 | Y | N | N | N |
| 1.25 | Y | Y | N | N |
| 2.5 | Y | Y | Y | N |
| 5.0 | Y | Y | Y | Y |

Y = Yes (detectable)
N = No (undetectable)

These results show that the foregoing protocol is suitable for checking glucose concentrations 0.035-5 mg/ml (at the dilution of the assay) if a visibility level at OD=0.10 is assumed. Table 4b retabulates the results to indicate this.

G.3. Determination of Cholesterol

Worthington Reagents catalog #27571 test kit for cholesterol was used to provide the cholesterol esterase and oxidase for the analyte specific reaction as well as the peroxidase and reagents for the indicator reaction. Varying levels of catalase were again used as indicator reaction. Thus, each reaction vessel contained:

199.5 units per ml cholesterol oxidase,
554.2 mU/ml cholesterol esterase,
19.6 μmole/ml sodium cholate,
4.1 μmole/ml 4-aminoantipyrine
2.2 units per ml peroxidase, and
3.28 μmol/ml phenol plus sufficient buffer and surfactant to maintain proper reaction conditions.

Each series contained catalase at 0, 625, 1250, 2500, 3750 units per ml. Cholesterol was supplied at 0, 1, 2, 3 and 5 ng/ml in the final reaction volume. Absorbance readings were taken at 500 nm after 2 minutes at 37° C., and are shown in Table 5 and FIG. 5, below. Absorbance readings were taken at 500 nm after 2 minutes at 37 KC, and are shown in Table 5:

TABLE 5

| Cholesterol Concentration | Catalase (units/ml) | | | |
| --- | --- | --- | --- | --- |
| ng/ml | 625 | 1250 | 2500 | 3750 |
| 1 | 0.062 | 0.013 | 0.012 | 0.004 |
| 2 | 0.110 | 0.014 | 0.011 | 0.009 |
| 3 | 0.161 | 0.033 | — | 0.012 |
| 4 | 0.234 | 0.044 | 0.029 | 0.015 |

FIG. 4 shows a graphic representation of these results. Comparison of this figure with the model set forth in FIG. 1 shows that the desired pattern is obtained.

G. 4. Assay on Solid Matrix Support

The assay of example ᶜ G.2 was repeated on a support using Whatman #2 filter paper as a matrix. Glucose oxidase reacts specifically with glucose to form peroxide, and the indicator reaction takes advantage of the catalysis by peroxidase of dye formation by reaction with H₂O₂. The competing reaction is the decomposition of H₂O₂ using catalase.

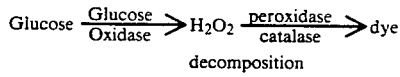

$$\text{Glucose} \xrightarrow{\text{Glucose Oxidase}} H_2O_2 \xrightarrow{\text{peroxidase}} \text{dye}$$
$$\text{catalase decomposition}$$

As in ᶜ G.2, the specific analyte reaction and indicator reaction components were supplied by the Worthington Stazyme Glucose (500 nm) kit.

Reagent was made for the dry kit reagents in combination with catalase solution such that a 15 ml spot would contain:

0.028 U glucose oxidase
0.02 μmol 4-aminoantipyrine
0.88 μmol Na p-hydroxybenzoate
0.02 U peroxidase
with pH 7 buffer;

and amounts of catalase varying from 9-187 units catalase. Glucose amounts applied varied between 3.1 μg and 50 μg. The reagent was applied in 15 μl spots, allowed to dry, 10 μl glucose then applied and the resulting color ranged on a scale of 0-10 as follows: wherein 1 is a trace color, 2 is visible purple color, 4 is moderate, 7 is intense and 10 is very intense. The papers were read after 3 minutes.

Assuming a yes-no cut-off between 1 and 2, and using 10 catalase concentrations in the range given above, the following results were obtained:

| Glucose Concentration in Applied Sample mg/ml | Ratio of Yes/No |
| --- | --- |
| 0.31 | 1/9 |
| 0.62 | 4/6 |
| 1.25 | 7/3 |
| 2.5 | 8/2 |
| 5.0 | 10/0 |

Thus, in the foregoing ranges, the pattern of results clearly distinguishes between the various glucose concentrations.

Changing the catalase concentration to the range 12.5-150 units in another Experiment "B" and to the range of 10-83 units in an Experiment "C" respectively produced similar results but with a higher desired visibility cut-off. Thus, for papers read after two hours and one hour respectively using a similar procedure to that above, but scoring respectively 4 as a yes, and <4 as no in Experiment B and 3 as a yes and <3 as a no, in Experiment C the following patterns were obtained:

| Glucose Concentration in Applied Sample | Y/N Ratio | |
| --- | --- | --- |
| mg/ml | Expt B | Expt C |
| 0.31 | 1/6 | 2/5 |
| 0.62 | 1/6 | 3/4 |
| 1.25 | 2/5 | 5/2 |
| 2.5 | 4/3 | 7/0 |
| 5.0 | 5/2 | 7/0 |

Thus, the required digital pattern is obtainable using "dry chemistry" with a solid support.

G.5. Solid Matrix Supported Reaction for Glucose Detection with Hexokinase Competition In a manner similar to that set forth in E.4, determinations of glucose were made except that hexokinase/ATP mixtures were substituted for catalase as the competing reaction. The results were scored as above. HK was supplied in amounts over the range 1-17 IU/ml; the ATP was added in fixed amount (170 μg) along with the components for the indicator reaction.

When read after 1 hour at room temperature, assuming visibility at 3 (yes) and no visibility at <3 (no), the results were as follows:

| Glucose Concentration in Sample Applied mg/ml | Ratio of Yes/No |
|---|---|
| 0.31 | 0/5 |
| 0.62 | 2/3 |
| 1.25 | 3/2 |
| 2.5 | 5/0 |
| 5.0 | 5/0 |

G.6. Determination of Creatine Phosphokinase-MB (Isoenzyme)

Heart tissue is known to contain creatine phosphokinase-MB isoenzyme, a form of creatine phosphokinase made up of M and B subunits. Brain tissue contains enzyme having 2 B subunits; most muscle tissue contains enzyme having 2M subunits. Antibodies may be prepared separately against the M and B forms.

Samples are analyzed for MB isoenzyme content as follows: a solid support containing anti-M antibodies and immobilized catalase is first prepared. Segments of the support are prepared by treating aminoethyl cellulose (AE-cellulose) with the proteins to be immobilized. The method used is as follows:

the AE-cellulose is washed with 0.5N NaOH, and then with water until pH 7 is approached. The washed solid is then incubated with a solution containing 50 mM phosphate buffer, pH 7; 3% wt/v glutaraldehyde; for 3 hr at room temperature. The AE-cellulose now containing bound glutaraldehyde is washed with 50 mM phosphate buffer, pH 7 to remove excess glutaraldehyde, and then incubated with a solution containing 50 mM phosphate, pH 7, 0.2 mg/ml BSA; 0.4 mg/ml anti-M antibody, and catalase at varying concentrations for the various segments in the range of 1,000-50,000 units/ml. This incubation is carried out for 24 hr at 4° C., and then the solid washed 3 times in 50 mM phosphate pH 7 containing 1N NaCl.

The segments are assembled into a linear array with increasing concentrations of catalase and mounted as a single solid support. The support is then contacted with a sample to be analyzed for the concentration of creatine phosphokinase-MB isoenzyme, for 15 min at 25° C. After washing with 0.1M phosphate, 0.2M NaCl, pH 7.2, the support is then incubated in a phosphate buffer solution containing 100 μg/ml anti-B antibodies conjugated to horseradish peroxidase (HRP). The conjugate is prepared as described by Wilson, M. B., et al, "Immunofluorescence and Related Staining Techniques", pp 215-224 (Knapp, W., (Ed.), Elsevier, Holland, N.Y. (1978)). This incubation is conducted at 25° C. for 15 min, and is followed by washing with 0.1M phosphate, 0.2M NaCl at pH 7.2. The solid is then contacted for 15 min at 25° C. with a substrate developer solution which contains 0.1M phosphate, pH 6.5, 1 mM 4-chloro-1-naphthal, and 0.03% wt/wt $H_2O_2$. The color generating dye, 4-chloro-1-naphthal forms an insoluble product which clings to the solid support to facilitate direct reading.

After incubation with the substrate developer solution, the solid support is dried, and read directly.

G.7. Determination of Biotin

Biotin is determined in samples using a protocol precisely identical with that set forth in Example 7 above, with the following exceptions. In preparing the specific affinity support, 0.5 mg/ml avidin is used in the incubation, rather than anti-M antibody; the HRP conjugate is prepared as a conjugate with avidin and is supplied to the support after treating with sample at a concentration of 50 μg/ml, in place of the anti-B used in Example 7. Again the color gradient can be visualized directly.

I claim:

1. A method to determine the concentration of analyte in a sample, which method comprises
    contacting the sample containing analyte with a solid support comprising a pattern of test portions wherein each of said test portions contains a preset amount of a first catalyst for providing a first catalytic reaction system and a preset amount of a first specific binding partner for said analyte, and wherein the ratio of said first catalyst to the specific binding partner is different in each of said test portions, so as couple said analyte to the support and
    coupling said solid support to a second catalyst for a second catalytic reaction system which competes with the first catalyst for the same substrate, whereby the amount of said second catalyst coupled to each said test portion is determined by the amount of said analyte coupled in said test portion, and
    wherein one of said two reaction systems leads directly or through subsequent reaction to a detectable result, followed by
    contacting said solid support with a substrate for the two competing catalysts, so as to obtain a pattern of detectable results which correlate to the concentration of analyte.

2. The method of claim 1 wherein said first and second catalysts are enzymes.

3. The method of claim 2 wherein the enzymes are catalase and peroxidase.

4. The method of claim 1 wherein said specific binding partner is an immunoglobulin or a fragment thereof.

5. The method of claim 1 which comprises the steps of
    contacting said solid support in a first step with sample containing analyte so as to couple said analyte to the support, followed by
    contacting said support with the second catalyst, said second catalyst being conjugated to a moiety capable of binding to the specific reaction partner, followed by
    contacting the solid support with substrate.

6. The method of claim 1 which comprises the steps of
    contacting said solid support with a sample containing analyte to which has been added said second catalyst coupled with a moiety which binds to said specific reaction partner in competition with analyte, followed by
    contacting said solid support with substrate.

7. The method of claim 1 which comprises the steps of contacting said solid support with a sample containing analyte so as to couple said analyte to the support, followed by contacting said support with the second catalyst coupled to a different specific binding partner capable of coupling to analyte, followed by contacting said solid support with substrate.

8. The method of claim 1 wherein said solid support further contains a second specific binding partner capable of coupling to said second catalyst and wherein said analyte is of sufficient bulk to block the second binding partner when bound to said first specific binding partner, which method comprises the steps of contacting said solid support with sample containing analyte so as to couple said analyte to the support, followed by contacting said solid support with said second catalyst followed by contacting said solid support with substrate.

9. The method of claim 1 wherein said solid support further contains a second specific binding partner capable of coupling to the second catalyst, wherein said method comprises contacting the solid support with a sample containing analyte to which has been added additional analyte conjugated to a bulk-conferring substituent which additional analyte competes with analyte for said first specific binding partner; followed by contacting the solid support with said second catalyst, followed by contacting the support with substrate.

* * * * *